United States Patent [19]
Fleming et al.

[11] Patent Number: 5,223,484
[45] Date of Patent: Jun. 29, 1993

[54] PEPTIDE WHICH REGULATES WEIGHT GAIN IN MAMMALS

[75] Inventors: Patrick J. Fleming, Annapolis, Md.; Ute M. Kent, Great Falls, Va.

[73] Assignee: Georgetown University, Washington, D.C.

[21] Appl. No.: 616,910

[22] Filed: Nov. 21, 1990

[51] Int. Cl.$^5$ .................. A61K 37/00; C07K 5/00
[52] U.S. Cl. ................. 514/14; 514/909; 514/910; 530/327
[58] Field of Search ............ 514/909, 910, 14, 15, 514/16, 17; 530/327, 328, 329

[56] References Cited

U.S. PATENT DOCUMENTS 4,843,071  6/1989  Hohenwarter ............ 514/909

OTHER PUBLICATIONS

*Protein Seq. Data Anal* (1988) 1:363–373, Barker et al.
"Peptide Hormones", published Jun. 1976 by Univ. Park Press (London) pp 1–7, see entire article.
The Embo Journal, vol. 7, No. 9, issued 1988, M. S. Perin et al., "The Structure of Cytochrome b 561, a Secretory Vesicle Specific Electron Transport Protein", pp. 2697–2703. See entire article.

*Primary Examiner*—Merrell C. Cashion, Jr.
*Assistant Examiner*—Bennett Celsa
*Attorney, Agent, or Firm*—Oblon, Spivak, McClelland, Maier & Neustadt

[57] ABSTRACT

A dodecapeptide for regulating weight gain in mammals, as defined in the sequence:

CHHRKKGYADLY wherein C is cysteine, H is histidine, R is arginine, K is lysine, G is glycine, Y is tyrosine, A is alanine, D is aspartic acid and L is leucine; and the remaining amino acids are each independently glycine, alanine, valine, leucine, isoleucine, serine, threonine, cysteine, cystine, methionine, aspartic acid, glutamic acid, asparagine, glutamine, lysine hydroxylysine, histidine, arginine, phenylalanine, tyrosine, tryptophan, proline or hydroxyproline.

4 Claims, 5 Drawing Sheets

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Cys His His Arg Lys Lys Gly Tyr Ala Asp Leu Tyr
    1               5                          10

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
         Cys His His Arg Lys Lys
          1               5
```

(2) INFORMATION FOR SEQ ID NO:3:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:3:

```
         Gly Tyr Ala Asp Leu Tyr
          1               5
```

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:4:

```
         Arg Lys Lys Gly Tyr Ala
          1               5
```

(2) INFORMATION FOR SEQ ID NO:5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:5:

```
         Cys Xaa His Xaa Lys Xaa Gly Xaa Ala Xaa Leu Xaa
          1               5                   10
```

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:6:

```
         Cys His Xaa Xaa Lys Lys Xaa Xaa Ala Asp Xaa Xaa
          1               5                   10
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:7:

```
         Cys His His Xaa Xaa Xaa Gly Tyr Ala Xaa Xaa Xaa
          1               5                   10
```

(2) INFORMATION FOR SEQ ID NO:8:

(i) SEQUENCE CHARACTERISTICS:

(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:8:

Cys His His Arg Xaa Xaa Gly Tyr Xaa Xaa Xaa Xaa
1               5               10

(2) INFORMATION FOR SEQ ID NO:9:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:9:

Cys His His Arg Lys Xaa Gly Xaa Xaa Xaa Xaa Xaa
1               5               10

(2) INFORMATION FOR SEQ ID NO:10:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:10:

Cys Xaa Xaa Xaa Xaa Gly Tyr Ala Asp Leu Xaa
1               5               10

(2) INFORMATION FOR SEQ ID NO:11:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:11:

Cys His Xaa Xaa Xaa Gly Tyr Ala Asp Xaa Xaa
1               5               10

(2) INFORMATION FOR SEQ ID NO:12:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:12:

Xaa His Xaa Arg Xaa Lys Xaa Tyr Xaa Asp Xaa Tyr
1               5               10

(2) INFORMATION FOR SEQ ID NO:13:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:13:

```
    Cys Xaa His Xaa Lys Xaa Gly Xaa Ala Xaa Leu Tyr
    1               5                   10
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
    Cys His Xaa Xaa Lys Lys Gly Xaa Ala Xaa Leu Xaa
    1               5                   10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
    Cys Xaa His Xaa Lys Xaa Gly Xaa Ala Asp Xaa Tyr
    1               5                   10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
    Cys His His Arg Xaa Xaa Gly Tyr Ala Xaa Xaa Xaa
    1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
    Cys His Xaa Xaa Xaa Xaa Gly Tyr Ala Asp Leu Xaa
    1               5                   10
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
    Cys His Xaa Xaa Lys Lys Xaa Xaa Xaa Asp Leu Tyr
    1               5                   10
```

( 2 ) INFORMATION FOR SEQ ID NO:19:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

Cys His His Xaa Lys Xaa Xaa Tyr Ala Xaa Leu Xaa
1               5                       10

( 2 ) INFORMATION FOR SEQ ID NO:20:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Cys Xaa His Xaa Lys Xaa Gly Xaa Ala Asp Leu Tyr
1               5                       10

( 2 ) INFORMATION FOR SEQ ID NO:21:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Cys His Xaa Arg Gly Xaa Xaa Tyr Ala Asp Leu Tyr
1               5                       10

( 2 ) INFORMATION FOR SEQ ID NO:22:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Cys Xaa Xaa Xaa Lys Lys Gly Xaa Ala Asp Leu Tyr
1               5                       10

( 2 ) INFORMATION FOR SEQ ID NO:23:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Cys His His Xaa Xaa Lys Xaa Xaa Ala Asp Leu Tyr
1               5                       10

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Cys His His Arg Lys Xaa Gly Tyr Ala Xaa Xaa Xaa
1               5                   10

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Cys His His Xaa Xaa Lys Lys Xaa Ala Asp Leu Xaa
1               5                   10

( 2 ) INFORMATION FOR SEQ ID NO:26:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

Cys His Xaa Arg Lys Xaa Xaa Tyr Ala Xaa Leu Xaa
1               5                   10

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

Cys His His Arg Leu Xaa Gly Tyr Ala Asp Xaa Xaa
1               5                   10

( 2 ) INFORMATION FOR SEQ ID NO:28:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

Cys His Xaa Arg Xaa Lys Gly Xaa Ala Asp Xaa Tyr
1               5                   10

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

Cys His His Xaa Lys Lys Gly Xaa Xaa Asp Leu Tyr
1               5                   10

( 2 ) INFORMATION FOR SEQ ID NO:30:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:30:

Cys His Xaa Arg Lys Lys Gly Tyr Xaa Asp Xaa Tyr
1               5                   10

( 2 ) INFORMATION FOR SEQ ID NO:31:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:31:

Cys His His Arg Lys Xaa Xaa Tyr Ala Xaa Leu Tyr
1               5                   10

( 2 ) INFORMATION FOR SEQ ID NO:32:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:32:

Cys His His Xaa Xaa Lys Gly Xaa Ala Asp Leu Tyr
1               5                   10

( 2 ) INFORMATION FOR SEQ ID NO:33:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:33:

Cys His His Arg Lys Lys Gly Tyr Ala Xaa Xaa Xaa
1               5                   10

( 2 ) INFORMATION FOR SEQ ID NO:34:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:34:

Xaa His His Arg Lys Lys Gly Tyr Ala Asp Leu Xaa
1               5                   10

( 2 ) INFORMATION FOR SEQ ID NO:35:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:

Xaa Xaa His Arg Lys Lys Gly Tyr Ala Asp Leu Tyr
1               5                   10

( 2 ) INFORMATION FOR SEQ ID NO:36:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

Cys Xaa Xaa Arg Lys Lys Gly Tyr Ala Asp Leu Tyr
1               5                   10

( 2 ) INFORMATION FOR SEQ ID NO:37:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

Cys His His Arg Lys Lys Gly Tyr Ala Asp Leu Xaa
1               5                   10

( 2 ) INFORMATION FOR SEQ ID NO:38:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

Cys His His Xaa Xaa Lys Gly Tyr Ala Asp Leu Tyr
1               5                   10

( 2 ) INFORMATION FOR SEQ ID NO:39:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

Cys His His Arg Lys Lys Xaa Xaa Ala Asp Leu Tyr
1               5                   10

( 2 ) INFORMATION FOR SEQ ID NO:40:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

Cys Xaa His Arg Lys Lys Xaa Tyr Ala Asp Leu Tyr
1               5                   10

( 2 ) INFORMATION FOR SEQ ID NO:41:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:41:

Xaa His His Arg Lys Lys Gly Tyr Ala Asp Leu Tyr
   1               5                   10

( 2 ) INFORMATION FOR SEQ ID NO:42:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:42:

Cys Xaa His Arg Lys Lys Gly Tyr Ala Asp Leu Tyr
   1               5                   10

( 2 ) INFORMATION FOR SEQ ID NO:43:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:43:

Cys His His Xaa Lys Lys Gly Tyr Ala Asp Leu Tyr
   1               5                   10

( 2 ) INFORMATION FOR SEQ ID NO:44:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:44:

Cys His His Arg Lys Lys Xaa Tyr Ala Asp Leu Tyr
   1               5                   10

( 2 ) INFORMATION FOR SEQ ID NO:45:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:45:

Cys His His Arg Lys Lys Gly Tyr Xaa Asp Leu Tyr
   1               5                   10

( 2 ) INFORMATION FOR SEQ ID NO:46:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:46:

Cys His His Arg Xaa Lys Gly Tyr Ala Asp Leu Tyr
1               5                   10

( 2 ) INFORMATION FOR SEQ ID NO:47:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:47:

Cys His Arg Lys His Lys Gly Asp Leu Tyr Tyr Ala
1               5                   10

( 2 ) INFORMATION FOR SEQ ID NO:48:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:48:

Cys Arg Lys His His Lys Asp Gly Tyr Leu Tyr Ala
1               5                   10

( 2 ) INFORMATION FOR SEQ ID NO:49:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:49:

Tyr Arg Cys Ala Lys His His Lys Asp Gly Leu Tyr
1               5                   10

( 2 ) INFORMATION FOR SEQ ID NO:50:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:50:

Asp Leu Tyr Cys His Arg Lys His Lys Gly Tyr Ala
1               5                   10

( 2 ) INFORMATION FOR SEQ ID NO:51:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:51:

Ala Leu Tyr Asp Cys His His Arg Lys Lys Gly Tyr
1               5                   10

(2) INFORMATION FOR SEQ ID NO:52:

(i) SEQUENCE CHARACTERISTICS:
　　　　(A) LENGTH: 12 amino acids
　　　　(B) TYPE: amino acid
　　　　(D) TOPOLOGY: linear (ii) MOLECULE TYPE: peptide (xi) SEQUENCE DESCRIPTION: SEQ ID NO:52:

```
Arg Ala Tyr Cys Lys His His Lys Gly Tyr Asp Leu
 1               5                  10
```

(2) INFORMATION FOR SEQ ID NO:53:

(i) SEQUENCE CHARACTERISTICS:
　　　　(A) LENGTH: 12 amino acids
　　　　(B) TYPE: amino acid
　　　　(D) TOPOLOGY: linear (ii) MOLECULE TYPE: peptide (xi) SEQUENCE DESCRIPTION: SEQ ID NO:53:

```
Cys Lys His His Arg Lys His Tyr Tyr Ala Leu Asp
 1               5                  10
```

(2) INFORMATION FOR SEQ ID NO:54:

(i) SEQUENCE CHARACTERISTICS:
　　　　(A) LENGTH: 12 amino acids
　　　　(B) TYPE: amino acid
　　　　(D) TOPOLOGY: linear (ii) MOLECULE TYPE: peptide (xi) SEQUENCE DESCRIPTION: SEQ ID NO:54:

```
Gly Tyr Asp Leu Ala Tyr Lys Arg Lys His Cys His
 1               5                  10
```

(2) INFORMATION FOR SEQ ID NO:55:

(i) SEQUENCE CHARACTERISTICS:
　　　　(A) LENGTH: 15 amino acids
　　　　(B) TYPE: amino acid
　　　　(D) TOPOLOGY: linear (ii) MOLECULE TYPE: peptide (xi) SEQUENCE DESCRIPTION: SEQ ID NO:55:

```
Lys Arg Pro Leu Gln Ala Glu Glu Gln Ala Leu Ser Met Asp Phe
 1               5                  10                  15
```

(2) INFORMATION FOR SEQ ID NO:56:

(i) SEQUENCE CHARACTERISTICS:
　　　　(A) LENGTH: 20 amino acids
　　　　(B) TYPE: amino acid
　　　　(D) TOPOLOGY: linear (ii) MOLECULE TYPE: peptide (xi) SEQUENCE DESCRIPTION: SEQ ID NO:56:

```
Cys Ser Met Glu Gly Pro Ala Ser Pro Ala Arg Ala Pro Gly Ala Leu
 1               5                  10                  15
Pro Tyr Lys Lys
                20
```

PEPTIDE WHICH REGULATES WEIGHT GAIN IN MAMMALS

BACKGROUND OF THE INVENTION

1. Field of the Invention

The present invention relates to a peptide which regulates weight gain in mammals.

2. Description of the Background

Appetite-suppressant agents are known, largely those which are based upon or derived from amphetamine. In fact, amphetamine is the parent compound of all but one of the agents currently used for appetite-suppression. Due to the potential for abuse that many of these drugs present, however, the use of such agents in reducing weight is controversial among physicians. That the use of amphetamine and similar appetite-suppressant agents is controversial may be seen from the fact that these compounds are now under the control of the Bureau of Narcotics and Dangerous Drugs (BNDD). Amphetamine, methamphetamine and phenmetrazine are in BNDD Schedule II which is highly restrictive, whereas the others are in Schedules III and IV which are succeedingly less restrictive but still indicative of abuse potential.

Worst yet, even when these drugs are used to reduce weight, tolerance develops over a period of a few to several weeks. However, the mood elevation may be retained with steadily increasing doses, leading to psychological and physical dependency. The massive doses required to support severe dependency finally lead to irreversible peripheral and central nervous system damage.

Thus, it would be extremely desirable to obtain substances for regulating weight gain in mammals which avoid the disadvantages described above.

SUMMARY OF THE INVENTION

Accordingly, it is object of the present invention to provide a peptide which regulates weight gain in mammals.

It is also an object of the present invention to provide pharmaceutical compositions which contain the peptide of the present invention.

Accordingly, the above objects and others which will become apparent in view of the following disclosure, are provided by a peptide having the formula:

$$\alpha\beta\gamma\delta\epsilon\eta\theta\lambda\mu\pi\rho\sigma$$

wherein at least six of the amino acid residues are as defined in the sequential positions specified in the sequence (SEQ ID NO:1):

CHHRKKGYADLY wherein C is cysteine, H is histidine, R is arginine, K is lysine, G is glycine, Y is tyrosine, A is alanine, D is aspartic acid and L is leucine; and the remaining amino acids are each independently glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, tryptophan, proline or hydroxyproline.

DETAILED DESCRIPTION OF THE PREFERRED EMBODIMENTS

Figure 1:
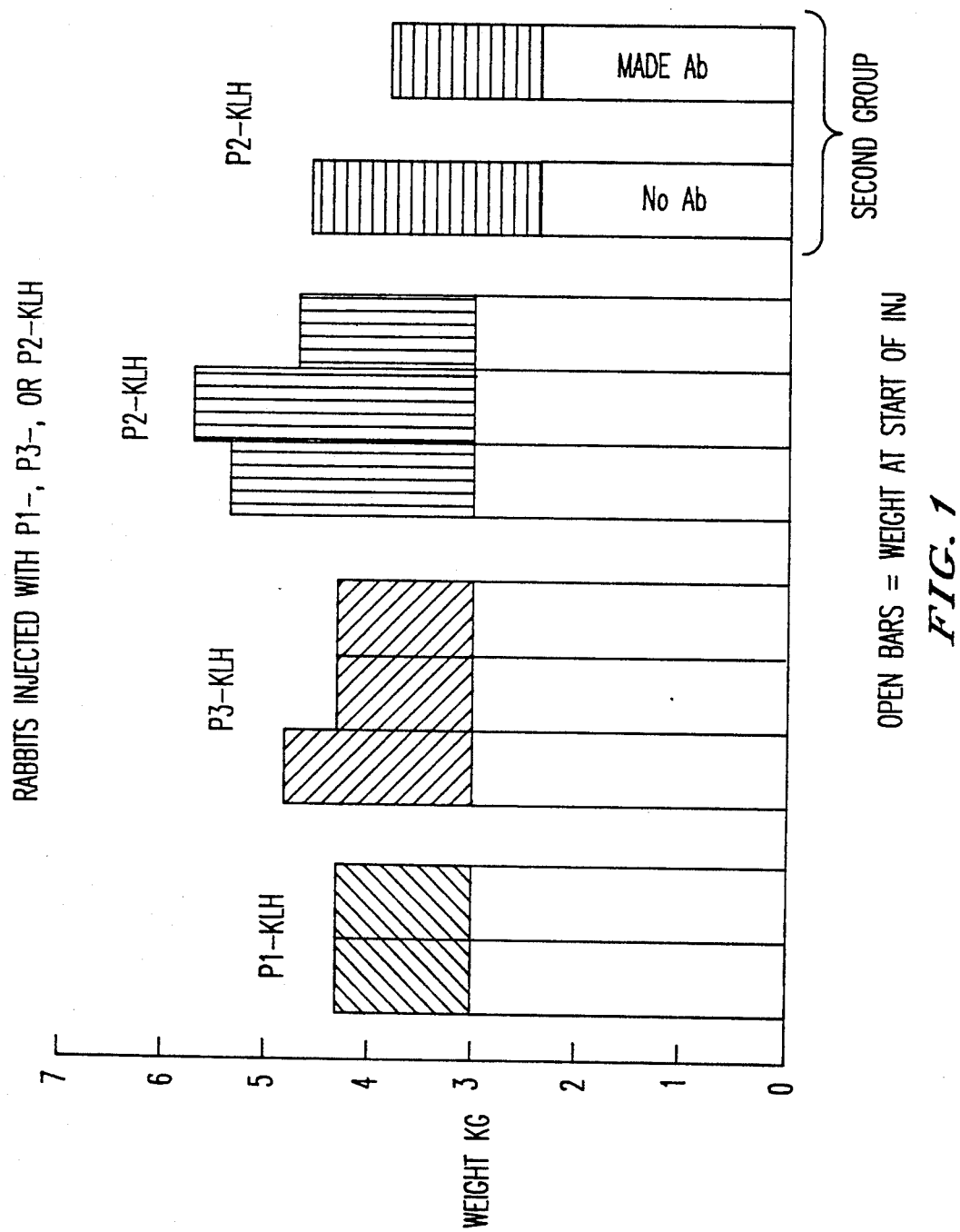
FIG. 1 illustrates the weights of rabbits before injection with the peptide of the present invention and at the end of 5 months.

In accordance with the present invention, a peptide is provided which is capable of regulating weight gain in mammals.

In accordance with the present invention, a peptide of the following formula is provided:

$$\alpha\beta\gamma\delta\epsilon\eta\theta\lambda\mu\pi\rho\sigma$$

wherein at least six of the amino acid residues are as defined in the sequential positions specified in the sequence (SEQ ID NO:1);

CHHRKKGYADLY wherein C is cysteine, H is histidine, R is arginine, K is lysine, G is glycine, Y is tyrosine, A is alanine, D is aspartic acid and L is leucine; and the remaining amino acids are each independently glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, tryptophan, proline or hydroxyproline.

Notably, for the generic description of the present peptide, letters of the Greek alphabet are used.

However, the peptide sequences of the present invention are defined relative to the peptide of the formula (SEQ ID NO:1):

CHHRKKGYADLY wherein the standard one-letter amino acid abbreviation is used, for example, whereby C is cysteine, H is histidine, R is arginine, K is lysine, G is glycine, Y is tyrosine, A is alanine, D is aspartic acid and L is leucine.

In the present specification, the letters of the Greek alphabet and the standard one-letter amino acid abbreviation is used. See, for example, *Organic Chemistry of Biological Compounds*, R. Barker at pp. 55–56 (Prentice Hall, 1971).

Thus, of interest are dodecapeptides having at least six of the specific residues described immediately above in their designated positions in the sequence CHHRKKGYADLY (SEQ ID NO:1).

For example, peptides of the following formula (SEQ ID NO:2) are noted:

$$\alpha\beta\gamma\delta\epsilon\eta\theta\lambda\mu\pi\rho\sigma$$

wherein
α is cysteine;
β is histidine;

γ is histidine;
δ is arginine;
ε is lysine;
η is lysine; and
θ, λ, μ, π, ρ and σ are each independently glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, tryptophan, proline or hydroxyproline.

Further, peptides of the following formula (SEQ ID NO:3) are noted:

αβγδεηθλμπρσ

θ is glycine;
λ is tyrosine;
μ is alanine;
π is aspartic acid;
ρ is leucine;
σ is tyrosine; and
α, β, γ, δ, ε and η are each independently glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, tryptophan, proline or hydroxyproline.

Moreover, peptides of the following formula (SEQ ID NO:4) are noted:

αβγδεηθλμπρσ

δ is arginine;
ε is lysine;
η is lysine;
θ is glycine;
λ is tyrosine;
μ is alanine; and
α, β, γ, π, ρ and σ are each independently glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, tryptophan, proline or hydroxyproline.

Thus, specifically contemplated is the peptide:

αβγδεηθλμπρσ wherein at least six of the amino acid residues are as defined and in the sequential position specified in the sequence (SEQ ID NO:1):

CHHRKKGYADLY wherein C is cysteine, H is histidine, R is arginine, K is lysine, G is glycine, Y is tyrosine, A is alanine, D is aspartic acid, and L is leucine; and the remaining amino acid residues are each independently glycine, alanine, valine, leucine, isoleucine, serine, threonine, cysteine, cystine, methionine, aspartic acid, glutamic acid, asparagine, glutamine, lysine, hydroxy lysine, histidine, arginine, phenylalanine, tyrosine, tryptophan, proline or hydroxy proline.

For example, the present peptide may have the formulae:
C-β-H-δ-K-η-G-λ-A-π-L-σ (SEQ ID NO:5) or
C-H-γ-δ-K-K-θ-λ-A-D-ρ-σ (SEQ ID NO:6), or
C-H-H-δ-ε-η-G-Y-A-π-ρ-σ (SEQ ID NO:7), or
C-H-H-R-ε-η-G-Y-μ-π-ρσ (SEQ ID NO:8), or
C-H-H-R-K-η-G-λ-μ-π-ρ-σ (SEQ ID NO:9), or
C-β-γ-ε-G-Y-A-D-L-σ (SEQ ID NO:10), or
C-H-γ-εη-G-Y-A-D-ρ-σ (SEQ ID NO:11), or
α-H-γ-R-ε-K-θ-Y-μ-D-ρ-Y (SEQ ID NO:12), In each of the above formulae, the Greek letters indicate amino acid residues as broadly defined above, i.e., any one of glycine, alanine, valine, leucine, isoleucine, serine, threonine, cysteine, cystine, methionine, aspartic acid, glutamic acid, asparagine, glutamine, lysine, hydroxy lysine, histidine, arginine, phenylalanine, tyrosine, tryptophan, proline or hydroxy proline; whereas the standard one-letter amino acid abbreviations are used for the remaining amino acid residues.

However, it is more preferred if at least seven of the amino acid residues of the sequence:

αβγδεηθλμπρσ are as defined and in the sequential position specified in the sequence (SEQ ID NO:1)

CHHRKKGYADLY wherein C is cysteine, H is histidine, R is arginine, K is lysine, G is glycine, Y is tyrosine, A is alanine, D is aspartic acid, and L is leucine, and the remaining three amino acid residues are each independently glycine, alanine, valine, leucine, isoleucine, serine, threonine, cysteine, cystine, methionine, aspartic acid, glutamic acid, asparagine, glutamine, lysine, hydroxy lysine, histidine, arginine, phenylalanine, tyrosine, tryptophan, proline or hydroxyproline.

Examples of peptides having at least seven of the specified amino acids are those having the formulae:
C-β-H-δ-K-η-G-λ-A-π-L-Y (SEQ ID NO:13), or
C-H-γ-K-K-G-δ-A-π-L-σ (SEQ ID NO:14), or
C-β-H-δ-K-η-G-λ-A-D-ρ-Y (SEQ ID NO:15), or
C-H-H-R-ε-η-G-Y-A-π-ρ-σ (SEQ ID NO:16, or
C-H-γ-δ-ε-η-G-Y-A-D-L-σ (SEQ ID NO:17, or
C-H-γ-δ-ε-η-G-Y-A-D-L-σ, or
C-H-γ-ε-K-K-θ-γ-μ-D-L-Y (SEQ ID NO:18), or
C-H-H-δ-K-η-θ-Y-A-π-L-σ (SEQ ID NO:19).

It is even more preferred if at least eight, nine, ten or eleven of the amino acid residues of the sequence;

αβγδεηθλμπρσ are as defined and in the sequential position specified in the sequence (SEQ ID NO:1)

CHHRKKGYADLY which is defined as above.

Examples of peptides having at least eight of the specified amino acids are those having the formula:
C-β-Hδ-K-η-G-λ-A-D-L-Y (SEQ ID NO:20), or
C-H-γ-R-G-η-θ-Y-A-D-L-Y (SEQ ID NO:21), or
C-β-γ-δ-K-K-G-λ-A-D-L-Y (SEQ ID NO:22), or
C-H-H-δ-ε-K-θ-λ-A-D-L-Y (SEQ ID NO:23), or
C-H-H-R-K-η-G-Y-A-π-ρ-σ (SEQ ID NO:24), or
C-H-H-δ-ε-K-K-λ-A-D-L-σ (SEQ ID NO:25), or
C-H-γ-R-K-η-θ-Y-A-π-L-σ (SEQ ID NO:26).

Examples of peptides having at least nine of the specified amino acids are these having the formulae:
C-H-H-R-K-η-G-Y-A-D-ρ-σ (SEQ ID NO:27), or
C-H-γ-R-ε-K-G-λ-A-D-ρ-Y (SEQ ID NO:28), or
C-H-H-δ-K-K-G-λ-μ-D-L-Y (SEQ ID NO:29), or C-H-γ-R-K-K-G-Y-μ-D-ρ-Y (SEQ ID NO:30), or
C-H-H-R-K-η-θ-Y-A-π-L-Y (SEQ ID NO:31), or
C-H-H-δ-ε-K-G-λ-A-A-D-L-Y (SEQ ID NO:32), or
C-H-H-R-K-K-G-Y-A-π-ρ-σ (SEQ ID NO:33)

Examples of peptides having at least ten of the specified amino acids are those having the formula:
α-H-H-R-K-K-G-Y-A-D-L-σ (SEQ ID NO:34), or
α-β-H-R-K-K-G-Y-A-D-L-Y (SEQ ID NO:35), or
C-β-γ-R-K-K-G-Y-A-D-L-Y (SEQ ID NO:36), or
C-H-H-R-K-K-G-Y-A-D-L-σ (SEQ ID NO:37), or
C-H-H-δ-ε-K-G-Y-A-D-L-Y (SEQ ID NO:38), or
C-H-H-R-K-K-θ-λ-A-D-L-Y (SEQ ID NO:39), or
C-β-H-R-K-K-θ-Y-A-D-L-Y (SEQ ID NO:40).

Examples of peptides having at least eleven of the specified amino acids are those having the formula:
α-H-H-R-K-K-G-Y-A-D-L-Y (SEQ ID NO:41), or
C-β-H-R-K-K-G-Y-A-D-L-Y (SEQ ID NO:42), or
C-H-H-R-K-K-G-Y-A-D-L-σ (SEQ ID NO:37), or
C-H-H-δ-K-K-G-Y-A-D-L-Y (SEQ ID NO:43), or
C-H-H-R-K-K-θ-Y-A-D-L-Y (SEQ ID NO:44), or
C-H-H-R-K-K-G-Y-μ-D-L-Y (SEQ ID NO:45), or
C-H-H-R-ε-K-G-Y-A-D-L-Y (SEQ ID NO:46).

Notably, all of the above specified examples of peptide sequences having at least six, seven, eight, nine, ten or eleven of the specified amino acids are provided solely for purposes of illustration and are not intended to be limitative.

It is most preferred, however, as noted above, if the peptide has the sequence (SEQ ID NO:1):

CHHRKKGYADLY wherein each residue is as defined previously.

The peptides of the present invention may be synthesized using a standard solid-phase amino acid synthesis or may be provided by the fermentation of recombinant microorganisms. For example, the peptides may be synthesized in accordance with U.S. Pat. Nos. 4,058,512 and 4,235,772 both of which are incorporated herein in the entirety.

The present peptide may also, as indicated above, be prepared by the fermentation of transformed microorganisms containing a synthetic gene which codes for the present peptide. Conventional techniques may be used for the synthesis of the appropriate gene and for the transformation of a host microorganism. As a host microorganism, E. coli, for example, may be used. See for example, Current Protocols in Molecular Biology (Wiley Interscience).

Additionally, the present dodecapeptide may be described, as a short peptide, in terms of its amino acid composition. That is, the present invention may be described in terms of both its amino acid sequence or its amino acid composition. Due to the importance of conformational structure for large peptides in determining peptide activity, the amino acid sequence of large peptides is usually important in maintaining the activity. By contrast, however, for short peptides, activity may often be conserved merely by conserving the amino acid composition of the peptide without regard to sequence specificity. For example, see Barker, W. C. et al, Protein Seq. Data Anal.(1988) 1:363-373.

In accordance with the present invention, dodecapeptides are provided having the following amino acid composition: one cysteine residue, two histidine residues, one arginine residue, two lysine residues, one glycine residue, two tyrosine residues, one alanine residue, one aspartic acid residue, and a leucine residue, without regard to sequential order.

However, it is preferred if the two histidine residues are adjoining to each other, and independently the two lysine residues are adjoining to each other.

Thus, the present invention also provides a dodecapeptide having the following amino acid composition: one cysteine residue, two histidine residues, one arginine residue, two lysine residues, one glycine residue, two tyrosine residues, one alanine residue, one aspartic acid residue and a leucine residue, without regard to sequential order, the dodecapeptide having substantially the same activity as the dodecapeptide of the sequence (SEQ ID NO:1):

CHHRKKGYADLY wherein C is cysteine, H is histidine, R is arginine, K is lysine, G is glycine, Y is tyrosine, A is alanine, D is aspartic acid and L is leucine.

The phrase "substantially the same activity" is used herein to mean having at least 10% of the activity of the dodecapeptide of the sequence (SEQ ID NO:1):

CHHRKKGYADLY as measured by the effect on a μg of peptide per kg of mammalian body weight over a given period of time.

Thus, within the ambit of the above class of dodecapeptides are those whose sequence results from a scrambling of the sequence (SEQ ID NO:1):

CHHRKKGYADLY

For example, the following sequences are listed hereinbelow for purposes of illustration only and are not intended to be limitative:
CHRKHKGDLYYA (SEQ ID NO:47)
CRKHHKDGYLYA (SEQ ID NO:48)
YRCAKHHKDGLY (SEQ ID NO:49)
DLYCHRKHKGYA (SEQ ID NO:50)
ALYDCHHRKKGY (SEQ ID NO:51)
RAYCKHHKGYDL (SEQ ID NO:52)
CKHHRKGYYALD (SEQ ID NO:53)
GYDLAYKRKHCH (SEQ ID NO:54)

As with the other dodecapeptide sequences of the present invention, these sequences may be easily synthesized by solid-phase synthesis or prepared by recombinant DNA fermentation.

The present invention will now be further illustrated by reference to certain examples, which are provided solely for illustration and are not intended to be limitative.

EXAMPLE 1

Studies were initiated for the purpose of generating antibodies to several different sections of a protein called cytochrome b 561. This protein is a polypeptide of 273 amino acids. Several oligopeptides representing a different section of the cytochrome polypeptide were injected into rabbits in order to generate antisera against the specific sections of the cytochrome. The three peptides tested are those shown below in standard one-letter amino acid abbreviation:
P1(SEQ ID NO:55) (AA247-261) KRPLQA-EEQALSMDF
P2 (SEQ ID NO:1) (AA130-142) CHHRKKGYADLY P1 corresponds to the cytochrome b 561 carboxy-terminus amino acid sequence Lys(247) - Phe(261) (SEQ ID NO:55).

The internal peptide P2 (SEQ ID NO:1) contains amino acids His(130)-Tyr(142). A cysteine residue was added at the amino-terminus of P2 as a spacer and to facilitate coupling to carrier proteins.

P3 (SEQ ID NO:56) was composed of the amino-terminal cytochrome b 561 sequence Ser(21) - Tyr(37). A cysteine residue was added at the amino-terminus for coupling to carrier proteins and two lysine residues were added at the carboxy-terminus to increase solubility of the peptide.

These peptides were then coupled chemically to keyhole limpet hemocyanin, a carrier protein, to improve the immunogenicity in rabbits.

Each peptide/carrier conjugate (50 μg of peptide, approximately 30 nanomoles) was injected subcutaneously into three female rabbits (three groups of three rabbits, approximately 2 months old). Two weeks later the rabbits were injected again with the same amounts of peptide/carrier conjugate. Thereafter, each rabbit was injected with the conjugate at approximately monthly intervals and blood samples were drawn. After five months, the rabbits were sacrificed.

Before the first injection, the rabbits were weighed for calculation of anesthetic dose (used to sedate the rabbits during injection). Before the rabbits were sacrificed, they were weighed again as the rabbits which received P2 were quite obese compared to all other rabbits. The weights of the rabbits before injection and at the end of five months are shown in FIG. 1. The average weight of the five injected with peptides P1 and P3 was 4.4 kg. This is normal for adult female rabbits of this type at this age, i.e. the average weight expected at 6 months is 4.5 kg. However, the weights of the rabbits injected with peptide P2 averaged 5.2 kg, approximately 20% higher.

Since no antibodies were made in rabbits injected with P2 (the ones which appeared obese), two more rabbits were tested. These rabbits were younger, weighing only 2.4 kg at the beginning and the experiment was carried out for an additional two months. Therefore, these rabbits were less than 4 months old when they were weighed and sacrificed. One of these rabbits did make antibodies against P2 peptide and this rabbit did not gain as much weight as the rabbit which did not make antibodies.

EXAMPLE 2

In order to obtain statistically significant data on the effects of peptide P2 on weight gain, another series of experiments using mice were performed. Three groups of five mice (BALB/c strain) were used.

The first group received injections of peptide P2, a second group received injections of P3 (as control), and a third group received injections of saline (as control). Free peptides were used to avoid the possibility that the effect observed in Example 1 may have been due to the nature of the chemical coupling to the carrier protein.

Figure 2:
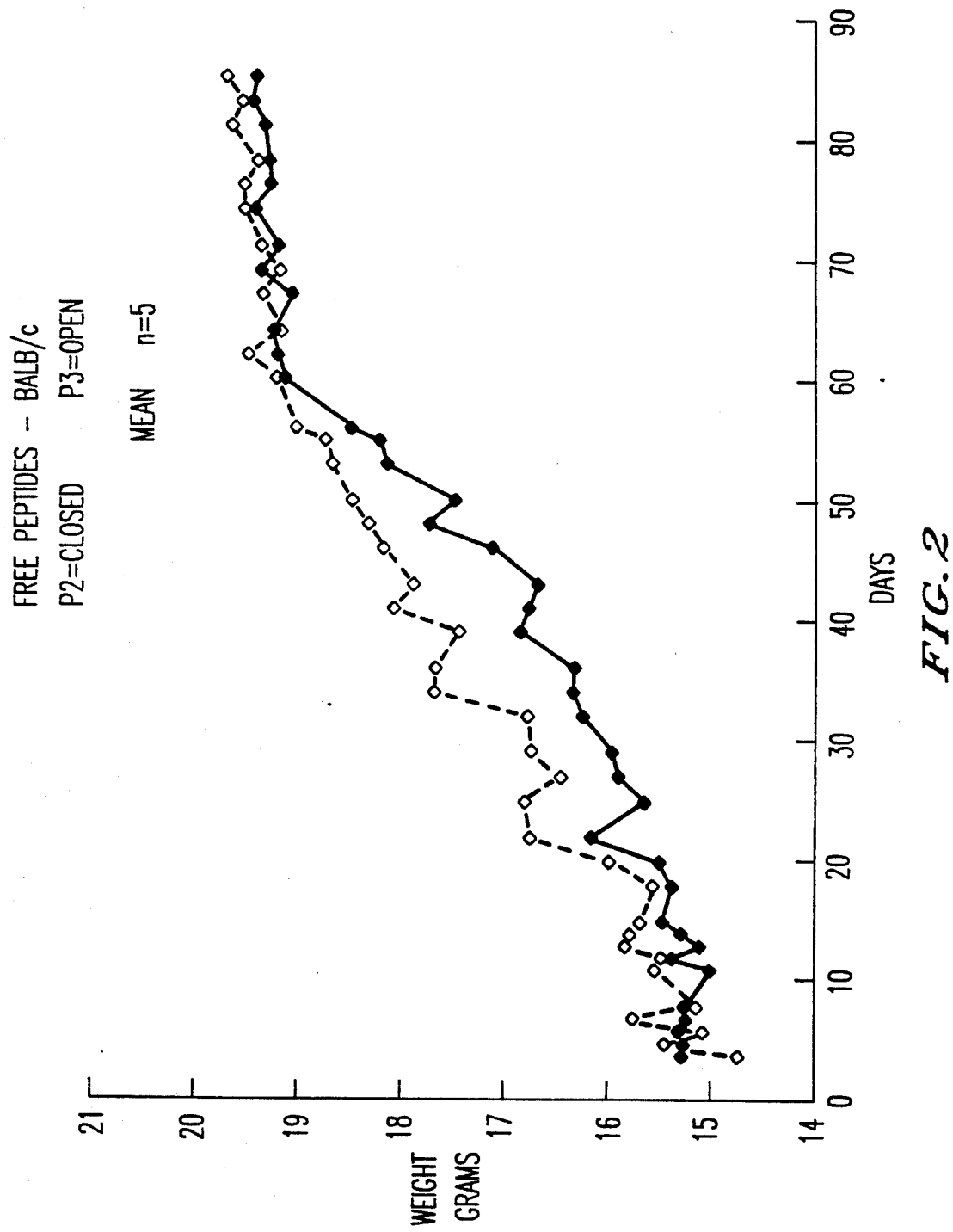
FIG. 2 illustrates average weight gain for groups of mice receiving either the peptide of the present invention or another comparative peptide.

Each mouse (weighing approximately 15 grams) received an injection of 2.5 μg (1.5 nanomoles) of peptide or saline injected subcutaneously. The mice were weighed three times per week and injected once per week with another 2.5 μg of peptide or saline. After 85 days the mice were sacrificed. The average weight gain for the groups of mice receiving either P2 or P3 peptides is shown in FIG. 2.

Figure 3:
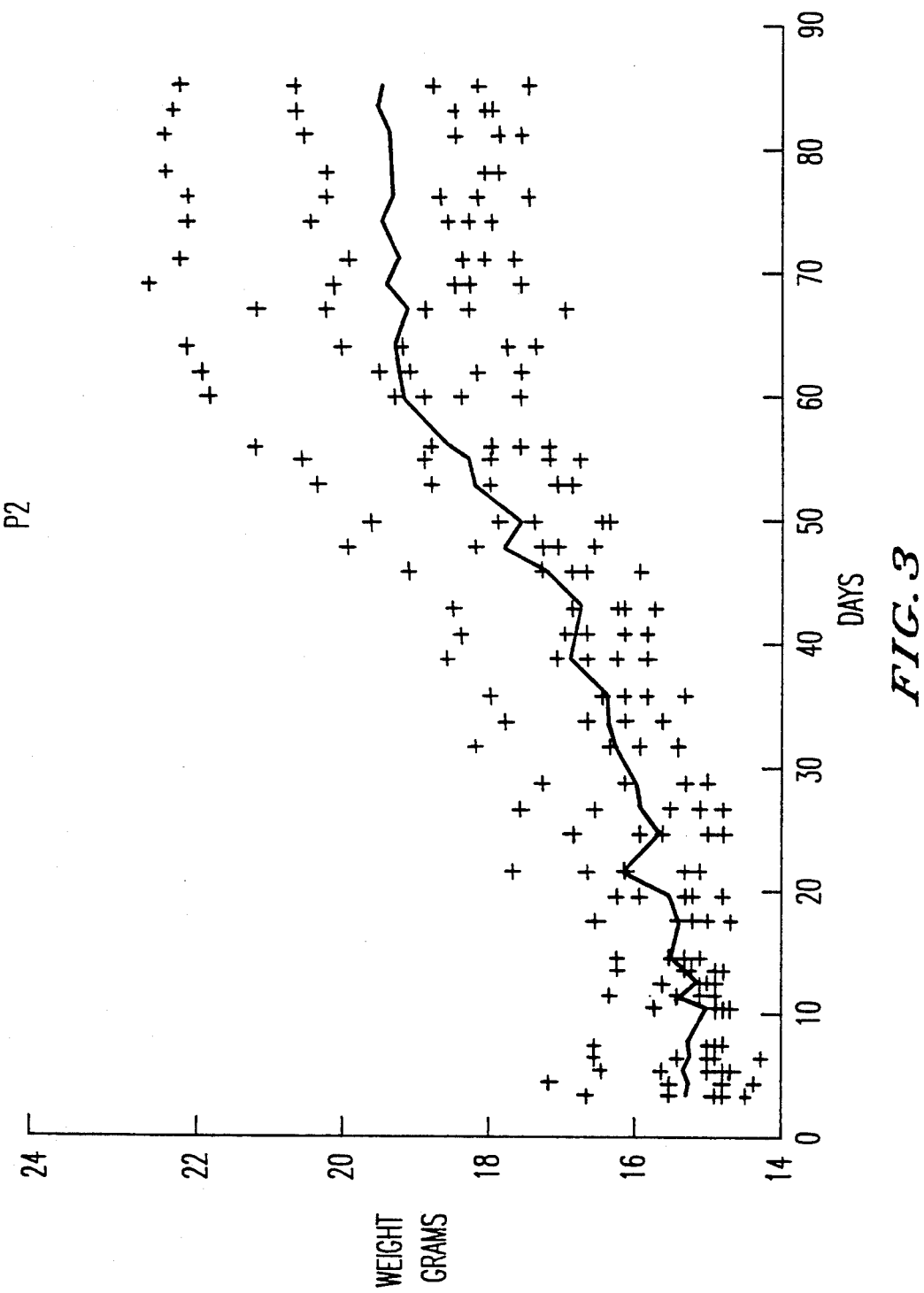
FIGS. 3 and 4 illustrate the delay in weight gain for mice treated with the peptide of the present invention as compared to a comparative control group.
Figure 4:
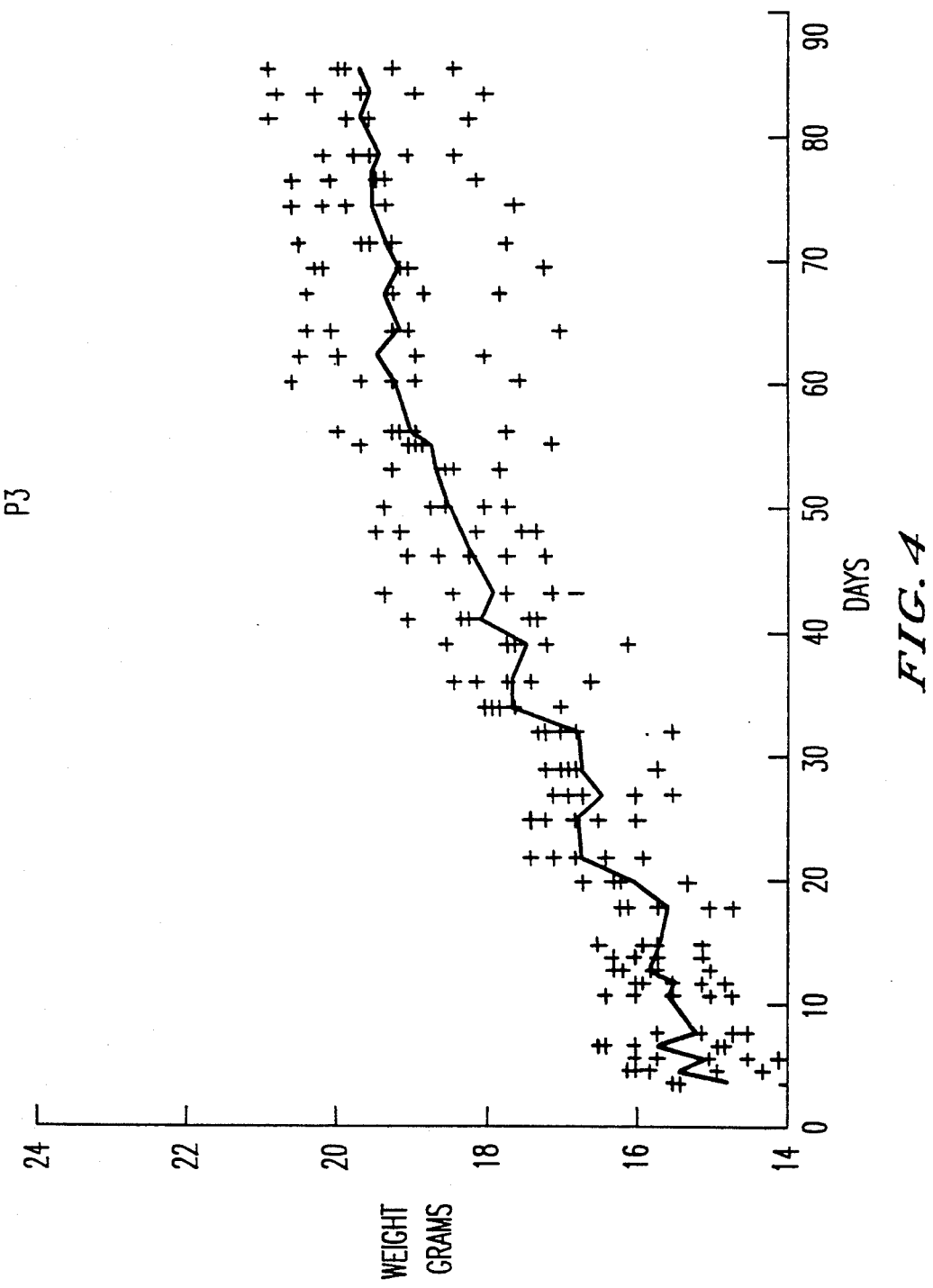
Figure 5:
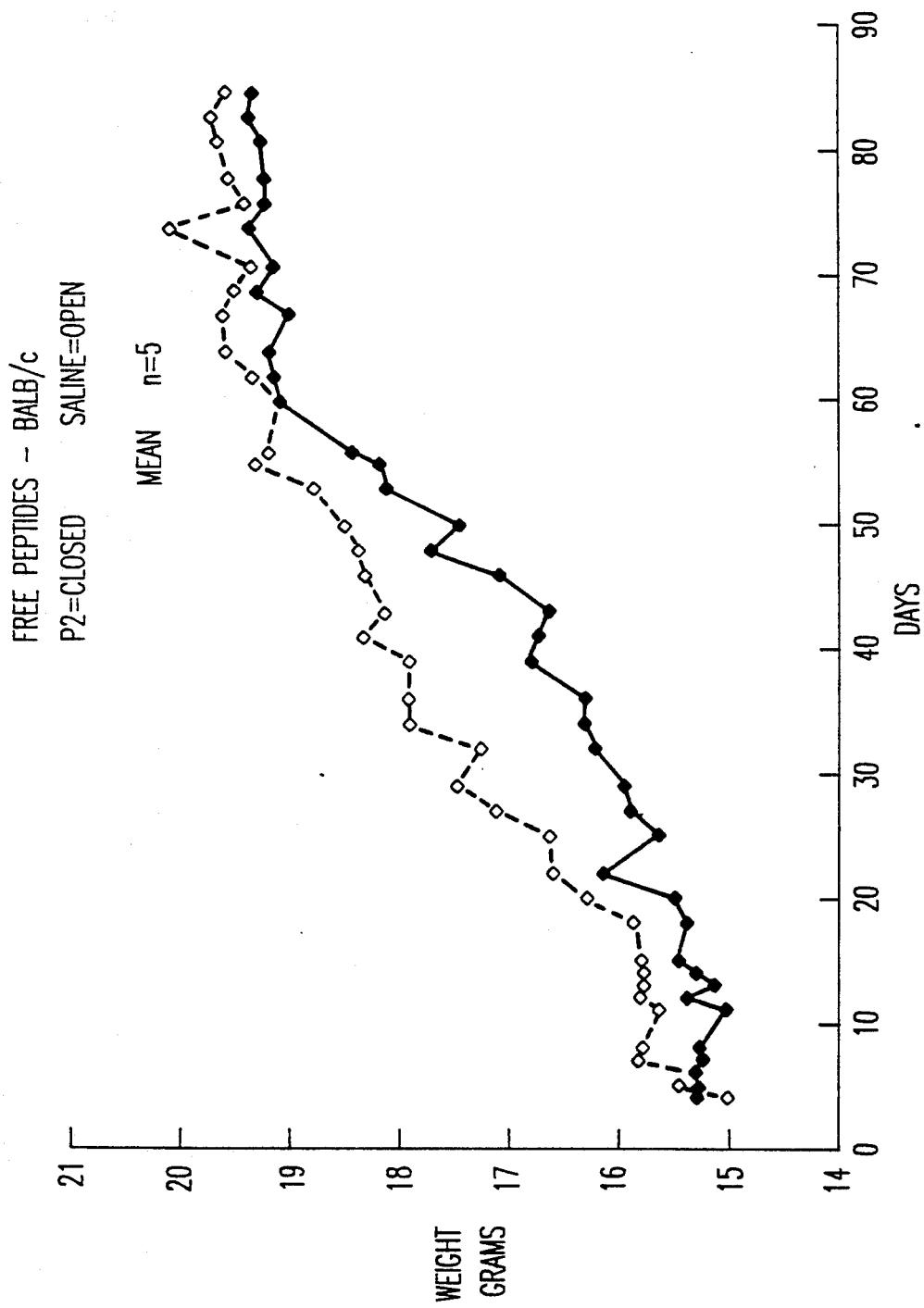
FIG. 5 illustrates the absence of a delay in weight gain for a group of mice treated with a saline control.

The P2 peptide delayed weight gain in these mice compared to the control P3 peptide group. However, after 60 days both groups were similar and stayed similar until day 85. FIGS. 3 and 4 show that even though individual mice varied significantly in their weight every member of the P2 group showed the delay in weight gain compared to the P3 control group. FIG. 5 shows that the saline control group did not show a delay in weight gain and was, in fact, not different than the P3 control group.

The above experiments indicate that mice appear to have the opposite response compared with rabbits when both types of animals are injected with peptide P2. Rabbits seem to gain weight and mice appear to have an inhibition of weight gain. Moreover, the effect of peptide P2 on the mice is to delay normal weight gain up to the end of the second month of weekly peptide administration. However, after the second month normal weight gain is observed. This may be caused by the development of antibodies to the peptide after this period of time. This latter phenomenon appears to be caused by a developmentally specific effect of the peptide or the mice may develop antibodies to the peptide after 60 days of weekly administration and these antibodies may inhibit the effect of the peptide.

Equivalent to the present peptides, for purposes of the present invention, are peptides of the formula:

X–(CHHRKKGYADLY)–Z wherein X and Z are each independently of the other hydrogen or from 1 to 1,000 amino acid residues, and which exhibit the activity of the present peptide or substantially the same activity as the present peptide.

As the amino acid residues, any of the following may be used independently for each of X and Z: glycine, alanine, valine, leucine, isoleucine, serine, threonine, cysteine, cystine, methionine, aspartic acid, glutamic acid, asparagine, glutamine, lysine, hydroxylysine, histidine, arginine, phenylalanine, tyrosine, tryptophan, proline and hydroxyproline. The amino acid sequences for each of X and Y may independently be random, block or even long repeating in nature.

The sequence (SEQ ID NO;1) CHHRKKGYADLY may be expected to be active as a part of a larger polypeptide as it is well known to those skilled in the art that the functional part of a protein, particularly a protein involved in binding, can reside in a short sequence of the total polypeptide.

Also equivalent to the present peptides, for purposes of the present invention, are peptides of the general formula:

X–(αβγδεηθλμπρσ)–Z wherein at least six and up to and including twelve of the amino acid residues α, β, γ, δ, ε, η, θ, λ, μ, π, ρ and σ are defined and in the sequential position specified in the sequence:

CHHRKKGYADLY wherein C is cysteine, H is histidine, R is arginine, K is lysine, G is glycine, Y is tyrosine, A is alanine, D is aspartic acid, and L is leucine, and the remaining amino acids are each independently glycine, alanine, valine, leucine, isoleucine, serine, threonine, cysteine, cystine, methionine, aspartic acid, glutamic acid, asparagine, glutamine, lysine, hydroxy lysine, histidine, arginine, phenylalanine, tyrosine, tryptophan, proline or hydroxyproline; and X and Z are as defined above.

The dodecapeptide of the present invention may be administered by itself or as a component of a composition. Generally, whether administered by itself or as part of a composition, from about 10 μg to about 1,000 μg of peptide per kg of body weight of mammalian host is administered. The present peptide, either by itself or as part of a composition, may be administered to any mammal, such as mice, rabbits, dogs or cats, particularly humans, however.

In addition to the above range, lesser or greater amounts may be used.

The present peptide is water-soluble and is preferably administered either intravenously or subcutaneously. The peptide may be conveniently administered in dextrose 5% saline or in saline solution.

The present peptide may also be microencapsulated in a lipid vesicle in accordance with a conventional encapsulation technique well known to those skilled in the art.

Compositions containing the present peptide may also be used. The compositions will generally contain the peptide and a conventional pharmaceutically acceptable carrier known to those skilled in the art. Generally, however, it is preferred that liquid compositions be used which are suitable for intravenous or subcutaneous injection. Examples of liquid carriers are saline solution, dextrose 5% saline solution or water, all of which are suitable for injection.

When the above liquids are used for injection, particularly for humans, it is desirable, if not essential, that they be sterile so as to be suitable for injection.

In the liquid composition, the peptide may, in general, comprise from about $10^{-7}$ g to $10^{-3}$ g/g of liquid carrier. Concentrations less or greater than this may be used, however.

Additionally, it is noted that the present peptide may be administered in conjunction with other ingredients in the composition, such as, for example, hormones and vitamins.

In accordance with another aspect of the present invention, antibodies may be prepared against the present peptides using methodologies as described in U.S. Pat. Nos. 4,151,268, 4,197,237 and 4,123,431. Each and all of these patents are hereby incorporated in the entirety herein.

Further, monoclonal antibodies against the present peptides can be prepared using conventional methodologies. In turn, these monoclonal antibodies may be used to identify the present peptides to detect and quantify the present peptides, or even to purify the present peptides by immunoaffinity chromatography.

Additionally, in accordance with the present invention, antibodies may be used to attenuate the effect of the present peptide in a host.

Finally, it is noted that any number of techniques may be used, in accordance with the present invention, for rendering the present peptides immunogenic.

For example, the present peptides may be rendered immunogenic by conjugation with muramyl peptides as described in U.S. Pat. Nos. 4,639,512 and 4,461,761. Also, the present peptides may be rendered immunogenic by conjugation with other polypeptides as described in U.S. Pat. No. 4,812,554. Each of U.S. Pat. Nos. 4,639,512, 4,461,761 and 4,812,554 are incorporated herein in the entirety.

By raising antibodies to the present peptides, an assay procedure can be used for the peptides in accordance with known methodologies.

Having described the present invention, it will be apparent to one skilled in the art that many changes and modifications can be made to the embodiments described above without departing from the spirit and the scope of the present invention.

---

What is claimed as new and desired to be secured by Letters Patent of the United States is:

1. A dodecapeptide having the following amino acid sequence:

CHHRKKGYADLY (SEQ ID NO:1)

wherein C is cysteine, H is histidine, R is arginine, K is lysine, G is glycine, Y is tyrosine, A is alanine, D is aspartic acid and L is leucine.

2. A pharmaceutical composition for regulating weight gain in mammals, comprising:

a) an effective amount of a dodecapeptide having the following amino acid sequence:

CHHRKKGYADLY (SEQ ID NO:1)

wherein C is cysteine, H is histidine, R is arginine, K is lysine, G is glycine, Y is tyrosine, A is alanine, D is aspartic acid and L is leucine;

b) a pharmaceutically acceptable carrier.

3. A method for regulating weight gain in mammals, which comprises administering to said mammal an effective amount of dodecapeptide having the amino acid sequence:

CHHRKKGYADLY (SEQ ID NO:1)

wherein C is cysteine, H is histidine, R is arginine, K is lysine, G is glycine, Y is tyrosine, A is alanine, D is aspartic acid and L is leucine.

4. The method of claim 3, wherein said dodecapeptide is administered in the form of a pharmaceutical composition.

* * * * *